United States Patent
Mortier et al.

(10) Patent No.: US 6,332,893 B1
(45) Date of Patent: Dec. 25, 2001

(54) VALVE TO MYOCARDIUM TENSION MEMBERS DEVICE AND METHOD

(75) Inventors: Todd J. Mortier, Minneapolis; Cyril J. Schweich, Jr., St. Paul, both of MN (US)

(73) Assignee: Myocor, Inc., St. Paul, MN (US)

(*) Notice: Subject to any disclaimer, the term of this patent is extended or adjusted under 35 U.S.C. 154(b) by 0 days.

(21) Appl. No.: 08/992,316

(22) Filed: Dec. 17, 1997

(51) Int. Cl.$^7$ ........................................... A61F 2/24
(52) U.S. Cl. ..................... 623/2.36; 623/2.41; 623/2.1
(58) Field of Search .................... 623/2, 400, 2.1, 623/3, 3.1

(56) References Cited

U.S. PATENT DOCUMENTS

| | | | |
|---|---|---|---|
| Re. 34,021 | 8/1992 | Mueller et al. | 604/51 |
| 4,192,293 | 3/1980 | Asrican | 128/1 |
| 4,261,342 | * 4/1981 | Aranguren Duo | 623/2 X |
| 4,372,293 | 2/1983 | Vijil-Rosales . | |
| 4,409,974 | 10/1983 | Freedland | 128/92 |
| 4,536,893 | 8/1985 | Parravicini | 623/3 |
| 4,936,857 | 6/1990 | Kulik . | |
| 4,944,753 | 7/1990 | Burgess et al. | 623/16 |
| 4,960,424 | * 10/1990 | Grooters | 623/2 |
| 4,997,431 | 3/1991 | Isner et al. | 606/15 |
| 5,106,386 | 4/1992 | Isner et al. | 606/15 |

(List continued on next page.)

FOREIGN PATENT DOCUMENTS

| | | | |
|---|---|---|---|
| 36 14 292 C1 | * 11/1987 | (DE) | 623/2 |
| 42 34 127 A1 | * 5/1994 | (DE) | 623/2 |
| 0 583 012 | 2/1994 | (EP) . | |
| 91/19465 | * 12/1991 | (WO) | 623/2 |
| 95/06447 | 3/1995 | (WO) . | |
| 95/16476 | 6/1995 | (WO) . | |

(List continued on next page.)

OTHER PUBLICATIONS

Dickstein et al., "Heart Reduction Surgery: An analysis of the Impact on Cardiac Function," *The Journal of Thoracic and Cardiovascular Surgery,* vol. 113, No. 6, Jun. 1997, 9 pages.

McCarthy et al., "Early Results with Partial Left Ventriculectomy," From the Departments of Thoracic and Cardiovascular Surgery, Cardiology, and Transplant Center, Cleveland Clinic Foundation, Presented at the 77$^{th}$ Annual Meeting of the American Assocation of Thoracic Surgeons, May 1997, 33 pages.

Alonso–Lej, M.D., "Adustable Annuloplasty for Tricuspid Insufficiency," *The Annals of Thoracic Surgery,* vol. 46, No. 3, Sep. 1988, 2 pages.

A. Carpentier and J.C. Chachques, "Myocardial Substitution with a Stimulated Skeletal Muscle: First Successful Clinical Case", Letter to the Editor, p. 1267, Sep. 25, 1996.

C. David Ianuzzo et al., "Preservation of the Latissimus Dorsi Muscle During Cardiomyoplasty Surgery", *J. Card. Surg.,* 1996:11:99–108.

(List continued on next page.)

*Primary Examiner*—David H. Willse
(74) *Attorney, Agent, or Firm*—Finnegan, Henderson, Farabow, Garrett & Dunner, LLP

(57) ABSTRACT

A device for heart valve repair including at least one tension member having a first end and second end. A basal anchor is disposed at the first end of the tension member and a secondary anchor at the second end. The method includes the steps of anchoring the basal anchor proximate a heart valve and anchoring the secondary anchor at a location spaced from the valve such that the chamber geometry is altered to reduce heart wall tension and/or stress on the valve leaflets.

20 Claims, 7 Drawing Sheets

U.S. PATENT DOCUMENTS

| | | | |
|---|---|---|---|
| 5,131,905 | 7/1992 | Grooters | 600/16 |
| 5,169,381 | 12/1992 | Snyders | 600/16 |
| 5,192,314 | 3/1993 | Daskalakis | 623/3 |
| 5,250,049 | 10/1993 | Michael | 606/72 |
| 5,284,488 | 2/1994 | Sideris | 606/213 |
| 5,385,528 | 1/1995 | Wilk | 680/18 |
| 5,433,727 | 7/1995 | Sideris | 606/213 |
| 5,450,860 | 9/1995 | O'Connor . | |
| 5,452,733 | 9/1995 | Sterman et al. . | |
| 5,458,574 | 10/1995 | Machold et al. . | |
| 5,496,305 | 3/1996 | Kittrell et al. | 606/15 |
| 5,509,428 | 4/1996 | Dunlop | 128/898 |
| 5,533,958 | 7/1996 | Wilk | 600/18 |
| 5,571,215 | 11/1996 | Sterman et al. . | |
| 5,584,803 | 12/1996 | Stevens et al. . | |
| 5,593,424 | 1/1997 | Northrup, III . | |
| 5,682,906 | 11/1997 | Sterman et al. . | |
| 5,702,343 | 12/1997 | Alferness | 600/37 |
| 5,718,725 | 2/1998 | Sterman et al. . | |
| 5,800,334 | 9/1998 | Wilk . | |
| 5,800,528 | 9/1998 | Lederman et al. . | |
| 5,814,097 | 9/1998 | Sterman et al. . | |
| 5,849,005 | 12/1998 | Garrison et al. . | |
| 5,855,614 | 1/1999 | Stevens et al. . | |
| 5,957,977 | 9/1999 | Melvin . | |
| 5,984,857 | 11/1999 | Buck et al. . | |
| 6,024,756 | 2/2000 | Huebsch et al. . | |

FOREIGN PATENT DOCUMENTS

| | | |
|---|---|---|
| 96/04852 | 2/1996 | (WO) . |
| 96/40356 | 12/1996 | (WO) . |
| 97/24101 | 7/1997 | (WO) . |
| 98/03213 | 1/1998 | (WO) . |
| 98/18393 | 5/1998 | (WO) . |
| 98/26738 | 6/1998 | (WO) . |
| 98/32382 | 7/1998 | (WO) . |
| 99/13777 | 3/1999 | (WO) . |
| 99/44534 | 9/1999 | (WO) . |

OTHER PUBLICATIONS

C. David Ianuzzo et al., "Preconditioning of Skeletal Muscle: Application to Dynamic Cardiomyopolasty", Invited Commentary, *J. Card. Surg.*, 199611:109–110.

J.C. Chachques et al., "Latissimus Dorsi Dynamic Cardiomyoplasty", *Ann. Thorae. Surg.*, 1989:47:600–604.

L. Moreira et al., "Latissimus Dorsi Cardiomyoplasty in the Treatment of Patients with Dilated Cardiomyopathy", Supplement IV Circulation, Sep. 25, 1996, 7 pgs.

C. Lucas et al., "Long–Term Follow–Up (12 to 35 Weeks) After Dynamic Cardiomyoplasty", *JACC*, vol. 22, No. 3, Sep. 1993: 758–67.

R. Batista et al., "Partial Left Ventriculectomy to Improve Left Ventricular Function in End–Stage Heart Disease", *J. Card. Surg.*, 1996:11:96–98.

"Congestive Heart Failure in the United States: A New Epidemic" Data Fact Sheet, National Heart, Lung, and Blood Institute, National Institutes of Health, Dec. 9, 1996, pp. 1–6.

R. Kormos et al., "Experience with Univentricular Support in Mortally Ill Cardiac Transplant Candidates", *Ann. Thorac. Surg.*, 1990:49:261–71.

R. Wampler et al., "Treatment of Cardiogenic Shock with the Hemopump Left Ventricular Assist Device", *Ann. Thorac. Surg.*, 1991:52:506–13.

P. McCarthy et al., "Clinical Experience with the Novacor Ventricular Assist System", *J. Thorac Cardiovasc Surg.* 1991:102:578–87.

C. Burnett et al., "Improved Survival After Hemopump Insertion in Patients Experiencing Postcardiotomy Cardiogenic Shock During Cardiopulmonary Bypass", From the Section of Transplantation, Division of Cardiovascular Surgery, Texas Heart Institute and St. Luke's Episocopal Hospital, Houston, Texas, date even with or prior to Jan. 2, 1997, pp. 626–628.

S. Phillips et al., "Hemopump Support for the Faling Heart", From the Department of Cardiovascular Medicine and Surgery, Mercy Hospital Medical Center, Des Moines, Iowa, date even with or prior to Jan. 2, 1997, pp. 629–631.

G. Deeb et al., "Clinical Experience with the Nimbus Pump", From the University of Michigan Medical Center Section of Thoracic Surgery and Division of Cardiology, Ann Arbor, Michigan, date even with or prior to Jan. 2, 1997, pp. 632–636.

G. Bearnson et al., "Development of a Prototype Magnetically Suspended Rotor Ventricular Assist Device", *ASAIO Journal*, 1996, pp. 275–280.

N. Sakakibara et al., "A Muscle Powered Cardiac Assist Device for Right Ventricular Support: Total Assist or Partial Assist?", *Trans Am Soc Artif Intern Organs*, vol. XXXVI, 1990, pp. 372–375.

Medtronic, Inc. 1996 Annual Shareholders Report, 79 pages.

Abiomed, Inc. Annual Report 1996, 32 pages.

Press Release dated Sep. 16, 1996, "Abiomed Wins $8.5 Million Federal Contract to Quality its Artificial Heart for Human Trials", 5 pages.

Press Release dated Sep. 26, 1996, "Abiomed's Temporary Artifical Heart System Reaches 200 U.S, Medical Center Milestone", 1 page.

Press Release dated May 17, 1996, "Abiomed Receives FDA Approval to Expand Indications for Use of Cardiac Assist System", 1 page.

Press Release dated Oct. 3, 1995, "Abiomed Wins $4.35 Million Contract from the National Heart, Lung and Blood Institutes to Develop Implantable Heart Booster", 1 page.

Press Release dated Sep. 29, 1995, "Abiomed Wins NIH Grant to Develop Calcification–Resistant Plastic Heart Valve", 1 page.

Press Release dated Aug. 25, 1995, "Abiomed Wins Research Grant from NIH to Develop Suturing Instrument for Abdominal Surgery", 1 page.

Press Release dated Aug. 11, 1995, "Abiomed Receives Grant from NIH to Develop Disposable Bearingless Centrifugal Blood Pump", 1 page.

Press Release dated Jun. 9, 1995, "Abiomed Receives Grant from National Institutes of Health to Develop a Laser Welding Techniques for Tissue Repair", 1 page.

Press Release dated Apr. 27, 1995, "Abiomed Temporary Artifical Heart System Reaches 1,00 Patient Milestone; BVS–5000 in More Than 100 U.S. Medical Centers", 1 page.

"Reversible Cardiomyopathy", *Thoratec's Heartbeat*, vol. 10.2, Aug. 1996, 2 pages.

C. Tsai et al., "Surface Modifying Additives for Improved Device–Blood Compatibility", *ASAIO Journal*, 1994, pp. 619–624.

D. Farrar et al., "A New Skeletal Muscle Linear–Pull Energy Convertor as a Power Source for Prosthetic Support Devices", *The Journal of Heart & Lung Transplantation*, vol. 11, No. 5, Sep., 1992, pp. 341–349.

Brochure entitled "Thoratec Ventricular Assist Device System—Because Heart Patients Come in All Sizes", date even with or prior to Jan. 2, 1997, 3 pages.

Press Release dated Oct. 3, 1994, "Heartmate System Becomes First Implantable Cardiac–Assist Device to be Approved for Commercial Sale in the U.S.", 1 page.

E. Bocchi et al., "Clinical Outcome after Surgical Remodeling of Left Ventricle in Candidates to Heart Transplantation with Idiopathic Dilated Cardiomyopathy—Short Term Results", date even with or prior to Jan. 2, 1997, 1 page.

Bach, M et al., "Early Improvement in Congestive Heart Failure after Correction of Secondary Mitral Regurgitation in End–Stage Cardiomvopathy", *American Heart Journal*, Jun. 1995, pp. 1165–1170.

Schuler, G. et al., "Temporal Response of Left Ventricular Performance to Mitral Valve Surgery", vol. 59, No. 6, Jun. 1979, pp. 1218–1231.

Huikuri, H., "Effect of Mitral Valve Replacement on Left Ventricular Function in Mitral Regurgitation", *Br Heart F*, vol. 49, 1983, pp. 328–333.

Pitarys II., C. et al., "Long–Term Effects of Excision of the Mitral Apparatus on Global and Regional Ventricular Function in Humans", *JACC*, vol. 15, No. 3, Mar. 1, 1990, pp. 557–563.

Bolling, s. et al., "Surgery for Acquired Heart Disease/Early Outcome of Mitral Valve Reconstruction in Patients with End–Stage Cardiomyopathy", *The Journal of Thoracic and Cardiovascular Surgery*, vol. 109, No. 4, Apr. 1995, pp. 676–683.

Masahiro, O. et al., "Surgery for Acquired Heart Disease/ Effects of Preserving Mitral Apparatus on Ventricular Systolic Function in Mitral Valve Operations in Dogs", *The Journal of Thoracic and Cardiovascular Surgery*, vol. 106, No. 6, Dec. 1993, pp. 1138–1146.

Boyd et al., "Tricuspid Annuloplasty–Five and one–half years' experience with 78 patients", *The Annals of thoracic Surgery*, vol. 68, No. 3, Sep.; 1974, 8 pages.

Kurlansky et al., "Adjustable Annuloplasty for Tricuspid Insufficiency", *Ann. Thorac. Surgery*, vol. 44, No. 4, Oct. 1987, 3 pages.

Edie, M.D., "Surgical repair of single ventricle," *The Journal of Thoracic and Cardiovascular Surgery*, vol. 66, No. 3, Sep., 1973, pp. 350–360.

McGoon, M.D. et al., "Correction of the univentricular heart having two atrioventricular valves," *The Journal of Thoracic and Cardiovascular Surgery*, vol. 74, No. 2, Aug., 1977, pp. 218–226.

Lev, M.D., et al., "Single (Primitive) Ventricle," *Circulation*, vol. 39, May, 1969, pp. 577–591.

Westaby with Bosher, "Landmarks in Cardiac Surgery," 1997, pp. 198–199.

Shumacker, "Cardiac Aneurysms," *The Evolution of Cardiac Surgery*, 1992, pp. 159–165.

Feldt, M.D., "Current status of the septation procedure for univentricular hearet," *The Journal of Thoracic and Cardiovascular Surgery*, vol. 82, No. 82, No. 1, Jul., 1981, pp. 93–97.

Doty, M.D., "Septation of the univentricular heart," *The Journal of Thoracic and Cardiovascular Surgery*, vol. 78, No. 3, Sep., 1979, pp. 423–430.

Savage, M.D., "Repair of left ventricular aneurysm," *The Journal of Thoracic and Cardiovascular surgery*, vol. 104, No. 3, Sep., 1992, pp. 752–762.

Cox, "Left Ventricular Aneurysms: Pathophysiologic Observations and Standard Resection," *Seminars in Thoracic and Cardiovascular Surgery*, vol. 9, No. 2, Apr., 1997, pp. 113–122.

Melvin, "Ventricular Radius Reduction Without Resection: A Computational Analysis," *ASAIO Journal*, 45:160–165, 1999.

* cited by examiner

VALVE TO MYOCARDIUM TENSION MEMBERS DEVICE AND METHOD

BACKGROUND OF THE INVENTION

The present invention pertains generally to the field of heart valve repair. More specifically, the present invention pertains to a device and method for the reduction of myocardial wall tension and the repair of mitral valve insufficiency.

Dilated cardiomyopathy is often accompanied by mitral valve insufficiency. There are several reasons for the presence of mitral valve insufficiency associated with a dilated heart. First, chamber dilation and associated high wall stresses increase the diameter of the mitral valve annulus. Additionally, as the heart dilates, the positioning of the papillary muscles is altered. Papillary muscles and chordae in a dilated heart will have moved both radially away and down from the mitral valve. This rearrangement of the vascular apparatus and enlargement of the annulus prevent the valve from closing properly.

Currently mitral valve insufficiency is treated by either repairing or replacing the valve. Surgical procedures used to repair the valve including ring posterior annuloplasty which consists of sewing a C or D-shaped ring around the posterior leaflet of the mitral valve and drawing in the annulus, reducing its previously enlarged diameter. Another method is to approximate the anterior and posterior mitral leaflets (Alfieri repair) by placing one suture through the center of both leaflets. This gives the valve a figure 8-shaped appearance when the valve is opened. When the mitral valve is replaced, the original leaflets are removed and the chordae are cut. An artificial valve consists of mechanical or tissue leaflets suspended on struts attached to a metal stent, and is sutured into place on the mitral annulus.

It has been argued that valve repair is preferable to valve replacement if the leaflet-chordae-papillary connections can be maintained. Heart wall stress will increase if the chordae are cut during valve replacement. It has been shown that by severing the chordae there can be 30 percent (30%) reduction in chamber function. Mitral valve replacement has high mortality in very sick, chronic heart failure patients.

SUMMARY OF THE INVENTION

The present invention pertains to a device and method for mitral valve repair. The mitral valve is generally defined as its leaflets or cusps, but in reality, it actually consists of the entire left ventricle chamber. By creating an improved chamber geometry, both chamber and valve function will be improved. The device of the present invention and method for valve repair/replacement can include treatment for chronic heart failure by reducing left ventricular wall tension.

In one embodiment of the present invention, the valve repair device includes an elongate tension member having a first end and second end. The basal anchor is disposed at the first end and the secondary anchor is disposed at the second end.

The basal anchor could include a pad and annuloplasty ring or the like. Alternately an artificial heart valve could serve as the basal anchor.

Tension members can be substantially rigid or substantially flexible. The secondary anchor can include a hook-shaped papillary muscle tissue loop, screw-shaped tissue anchor or transmural anchor pad.

The method of the present invention providing a tension member having a first end and a second end. The tension member has a basal anchor at the first end and a secondary anchor at the second end. The basal anchor is anchored proximate to the valve such that the tension member is disposed in the chamber. The secondary anchor is anchored to a portion of the heart spaced from the basal anchor such that the tension member is under tension and the geometry of the chamber has been altered by placement of the tension member.

The basal anchor can include an artificial heart valve, annuloplasty ring or the like. The secondary anchor can be anchored to a papillary muscle or transmurally anchored.

More than one tension member can be used. Additionally, a transverse tension member can be placed across the chamber generally perpendicular to the other tension members to further alter the geometry of the heart, reducing wall stress and improving chamber performance.

DETAILED DESCRIPTION OF THE INVENTION

Figure 1:
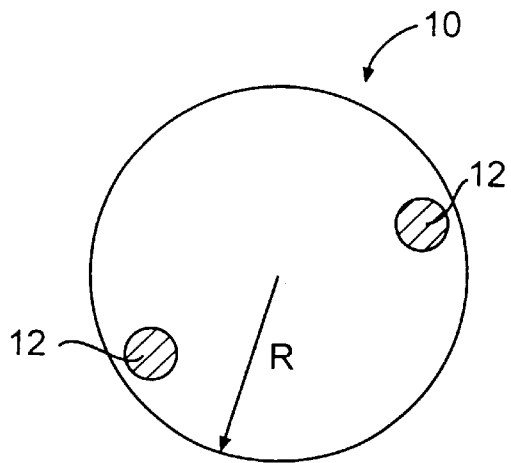
FIG. 1 is a transverse cross section of the left ventricle of a human heart taken from FIG. 2.
Figure 2:
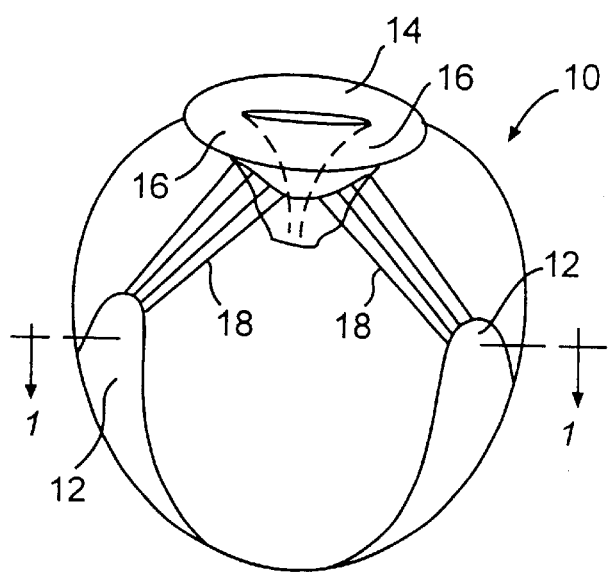
FIG. 2 is a vertical cross section of the left ventricle of a human heart.

Referring now the drawings wherein like reference numerals refer to like elements throughout the several views, FIG. 1 shows a transverse cross section of the left ventricle 10 of a failing heart taken from FIG. 2. The papillary muscles 12 are shown in cross section. FIG. 2 is a vertical cross section of human heart 10. A mitral valve is disposed near the top of left ventricle 10. Mitral valve 14 includes two leaflets or cusps 16. Chordae 18 extend between leaflets 16 and papillary muscles 12.

Figure 3:
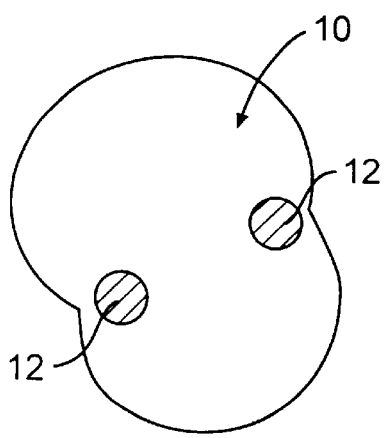
FIG. 3 is a modified, transverse, cross section of the left ventricle of a human heart taken from FIG. 4.
Figure 4:
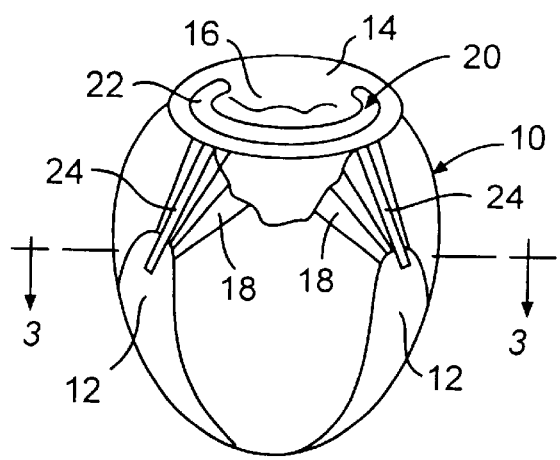
FIG. 4 is modified, vertical cross section of a human heart, modified by a device in accordance with the present invention.

FIG. 3 is a cross section of heart 10 modified from that shown in FIG. 1 by placement of valve repair device 20 in accordance with the present invention as shown in FIG. 4. FIG. 4 is a vertical cross section of left ventricle 10 with geometry modified by device 20. In this embodiment of the invention, device 20 includes a basal anchor 22 such as an annuloplasty or suture ring sewn proximate the annulus of valve 14. Extending from basal anchor 22 are elongate tension members 24. Each have a first end connected to basal anchor 22 and a second end anchored to papillary muscles 12 or the heart wall.

As can be seen in FIGS. 3 and 4, both the transverse radius and vertical dimension of left ventricle 10 has been reduced in comparison to that of FIGS. 1 and 2 by drawing papillary muscles 12 toward valve 14 with tension members 24. This change in geometry reduces heart wall stress and consequently increasing chamber function. Valve function is also improved as explained in more detail by reference to FIGS. 5 and 6.

Figure 5:
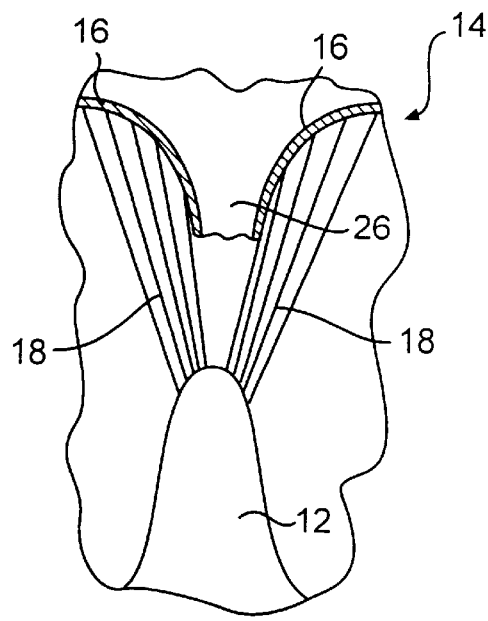
FIG. 5 is a cross section of an insufficient mitral valve of a left ventricle of a human heart.

FIG. 5 is a generally vertical cross section of an insufficient mitral valve of a heart suffering from chronic heart failure. In this case as the failing heart has dilated, papillary muscle 12 has been drawn away from mitral valve 14. The chordae connections between papillary muscles 12 and valve 14 in turn draws leaflets 16 apart such that during the normal cardiac cycle, leaflets 16 may not completely close. Thus, an opening 26 is left between leaflets 16 throughout the cardiac cycle. Opening 26 will allow blood to leak, reducing chamber efficiency.

Figure 6:
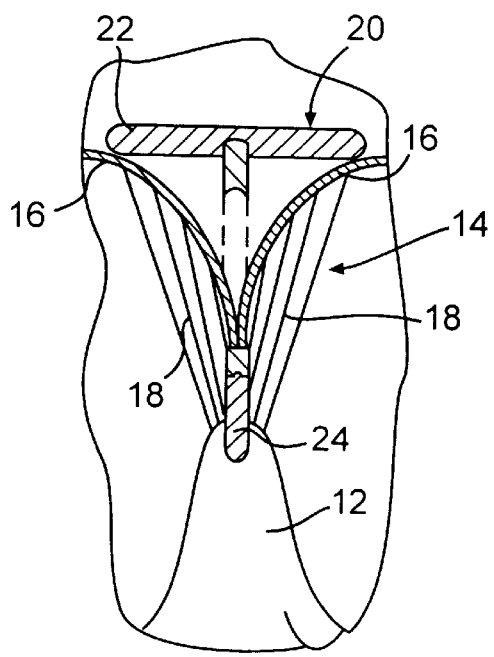
FIG. 6 is a cross section of a repaired valve and device in accordance with the present invention.

FIG. 6 is a view of the mitral valve 14 of FIG. 5 which has been modified by placement of valve repair device 20 as shown. Suture ring 22 is sewn proximate the annulus of valve 14, as known to those skilled in the use of suture rings. The annulus of valve 14 can be decreased in size by drawing the annulus toward the suture ring by the sutures used to connect ring 22 to the valve. Drawing the annulus of valve 14 toward suture ring 22 will help to eliminate opening 26. Tension member 24 is then anchored to papillary muscle 12 such that papillary muscle 12 is drawn toward valve 14. Whether or not the suture ring alone is sufficient to eliminate opening 26, drawing papillary muscle 12 toward valve 14 will provide additional stress relief on leaflet 16 promoting complete closure of valve 14. Drawing papillary muscle 12 toward valve 14 also reduces heart wall stress and increases chamber efficiency as discussed previously.

Figure 7:
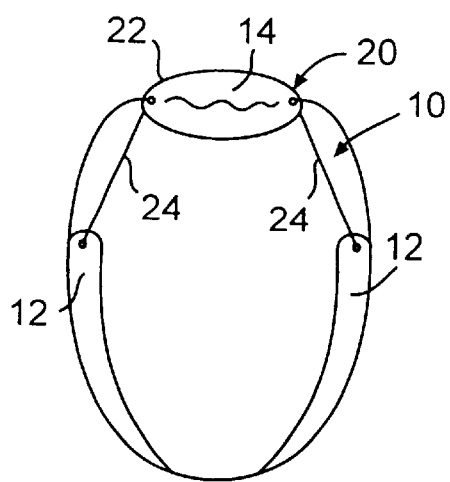
FIG. 7 is an embodiment of the device of the present invention.
Figure 8:
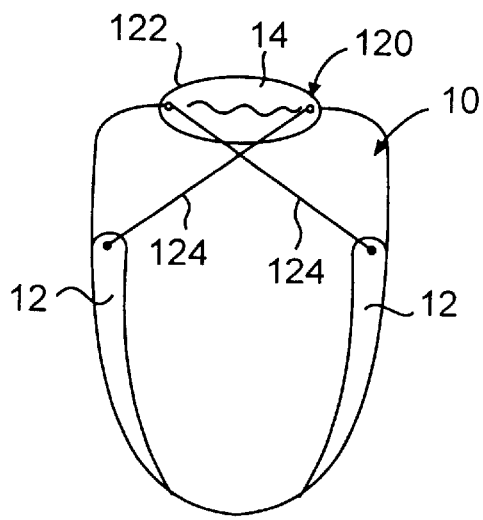
FIG. 8 is an alternate embodiment of a device in accordance with the present invention.

FIG. 7 is a highly simplified view of left ventricle 10 and valve repair device 20 as shown in FIG. 4. It can be noted that tension members 24 extend from basal anchor 22 to an adjacent papillary muscle 12. In contrast, FIG. 8 is a similar cross sectional view of left ventricle 10, but a valve repair device 120 is placed such that its tension members 124 extend between a basal anchor 122 and a papillary muscle 12 transversely opposite the point at which tension member 124 is connected to basal anchor 122. This arrangement, as opposed to that shown in FIG. 7, can increase the transverse component of the tension force in tension members 124 relative to the vertical component of that tensile force.

Figure 9:
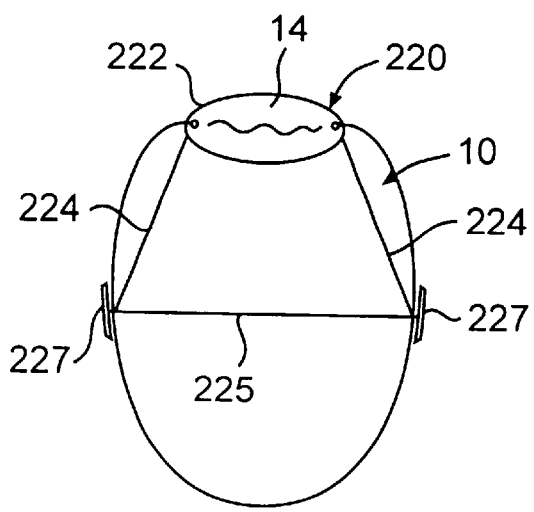
FIG. 9 is yet another alternate embodiment of a device in accordance with the present invention.

FIG. 9 shows yet another embodiment of the valve repair device in accordance with the present invention referred to by numeral 220. In this embodiment, device 220 is disposed in left ventricle 10 in a manner similar to that of device 20 shown in FIG. 7 in that tension members 224 of device 220 extend from a basal anchor 222 to an adjacent secondary anchor point. The secondary anchor point is established by transverse extension of a tension member 225 across left ventricle 10. Tension member 225 is anchored transmurally to the heart wall at its opposite ends by pads 227. In turn, tension members 224 are anchored or connected to tension member 225.

Tension member 225 can be used to further alter the geometry of left ventricle 10 in a manner disclosed in U.S. patent application Ser. No. 08/933,456, entitled "HEART WALL TENSION REDUCTION APPARATUS AND METHOD", which was filed on Sep. 18, 1997 and is incorporated herein by reference.

Figure 10:
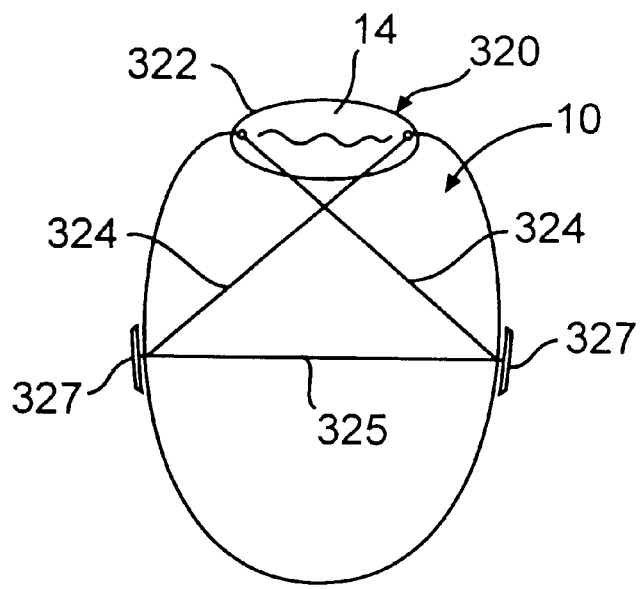
FIG. 10 is yet another alternate embodiment of the device in accordance with the present invention.

FIG. 10 shows yet another embodiment of a valve repair device in accordance with the present invention referred to by numeral 320. This embodiment includes a basal anchor 322 and tension members 324 and a transverse tension member 325 having anchor pads 327 similar to those of device 220. With respect to device 320, however, tension members 324 are crossed similar to those of device 120 of FIG. 8 to increase the horizontal component relative to the vertical component of the tensile force in tension member 324.

Figure 11:
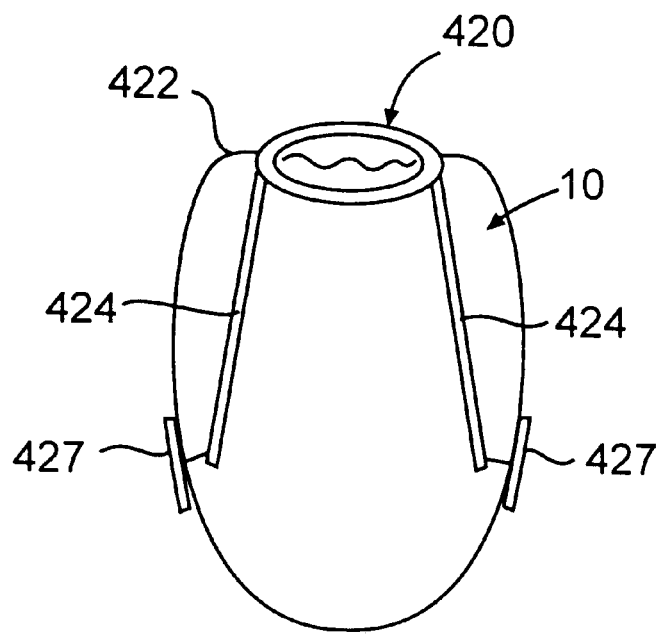
FIG. 11 is yet another alternate embodiment of a device in accordance with the present invention.

FIG. 11 is a yet another embodiment 420 of the valve repair device of the present method. Valve repair device 420 includes a basal anchor 422 and tension members 424. Tension members 424 are disposed in an arrangement similar to tension members 24 of device 20 shown in FIG. 7 except that tension members 424 are anchored transmurally by pads 427 rather than into papillary muscles 12. The relatively greater thickness of tension members 424 shown in FIG. 11, as compared to tension members 24 shown in FIG. 7, merely illustrates that the tension members can be substantially rigid or in the case of tension members 24, substantially flexible. It should be understood, however, that in any of the embodiments shown herein, the tension members could be advantageously formed to be substantially flexible or substantially rigid.

Figure 12:
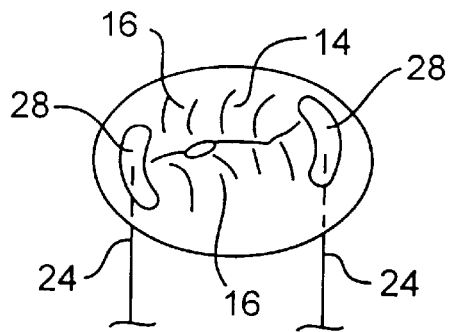
FIG. 12 is a view of a basal anchor for the device of the present invention.

FIG. 12 is a top or posterior view of valve 14. In this embodiment, the basal anchor for the valve repair device is shown as discrete pads 28 which can be sewn to the posterior side of valve 14. Tension members 24 are shown extending from respective pads 28 into the left ventricle.

Figure 13:
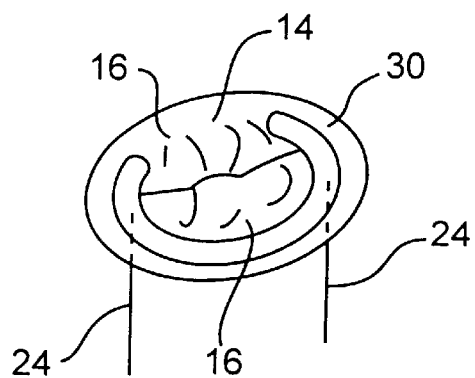
FIG. 13 is a suture ring serving as a basal anchor for the device of the present invention.

FIG. 13 is the same view of valve 14 as FIG. 12. In FIG. 13, however, the basal anchor 22 is shown as a crescent-shaped suture ring. Tension members 24 extends from basal anchor 22 through valve 14 into the left ventricle.

Figure 14:
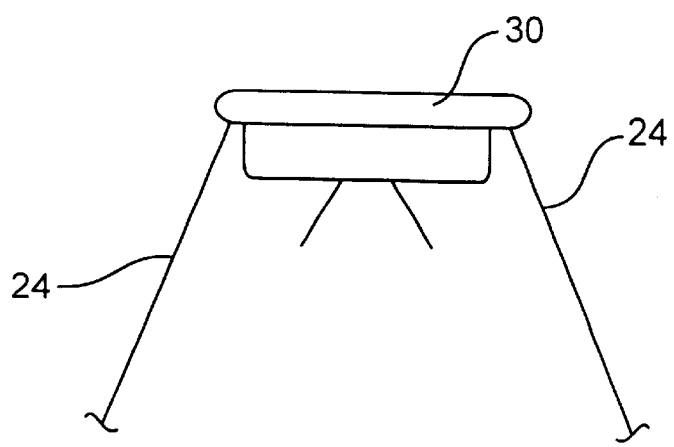
FIG. 14 is a replacement valve serving as a anchor for the device of the present invention.

FIG. 14 is a side view of an artificial heart valve 30. If it is necessary to replace the valve rather than merely repair it, artificial valve 30 can be used as a basal anchor for tension members 24.

Figure 15:
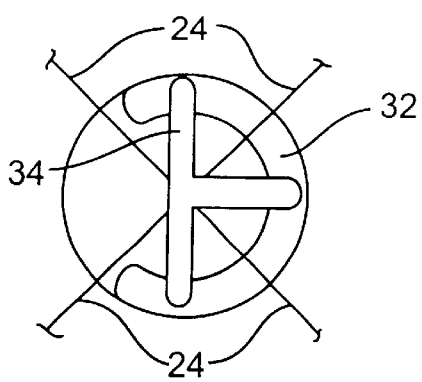
FIG. 15 is a top view of an alternate embodiment of a suture ring acting as an anchor for the device of the present invention.
Figure 16:
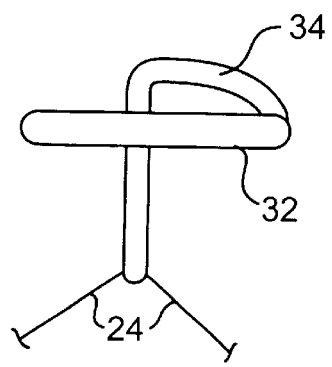
FIG. 16 is a side view of the suture ring of FIG. 15.

FIG. 15 is a top view of an alternate embodiment of a suture ring basal anchor 32. Ring 32 has a crescent shape and a pylon 34 extending through the mitral valve. FIG. 16 is a side view of suture ring 32 showing tension members 24 attached to pylon 34.

Tension members 24 preferably extend through the tissue of valve 14 rather than through the valve opening. It can be appreciated, however, that tension members 24 could be disposed through the valve opening. In the case of the embodiment of FIGS. 15 and 16, however, pylon 34 would be disposed through the valve opening. Tension members 24 associated with pylon 34 would be disposed on the opposite side of valve 14 from suture ring 32. Pylon 34 would preferably be disposed through the valve opening rather than the tissue forming valve 14.

Figure 17:
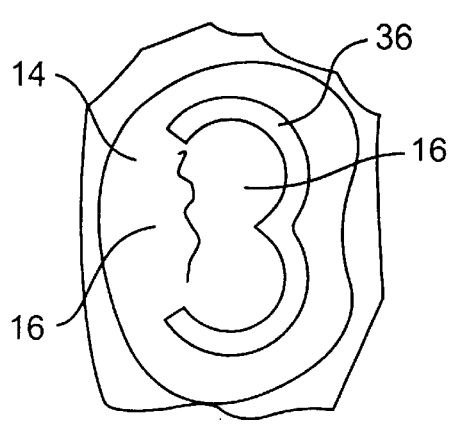
FIG. 17 is a view of an alternate embodiment of a suture ring which can act as basal anchor for the device of the present invention.
Figure 18:
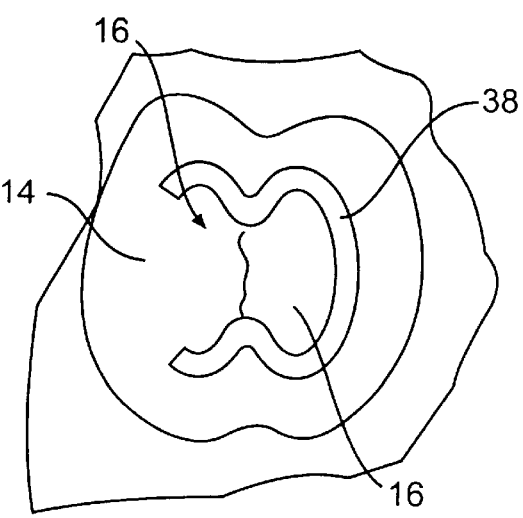
FIG. 18 is a view of yet another alternate embodiment of a suture ring which can act as a basal anchor for the present invention.

FIGS. 17 and 18 are yet additional alternate embodiments of suture rings which can be used as basal anchors in accordance with the present invention. The shape of the rings is selected such that as they are sewn into place on valve 14, the sutures can be used to draw tissue toward the inside of the ring, thus reducing the transverse and/or vertical cross sectional area of the associated heart chamber. This will advantageously reduce heart wall stress which is of particular benefit if the patient has a failing heart.

It can be appreciated that tension members 24 can be fixably or releasably attached to the basal anchor. Preferably, the tension members are fixably attached to the basal anchor during the valve repair procedure.

Figure 19:
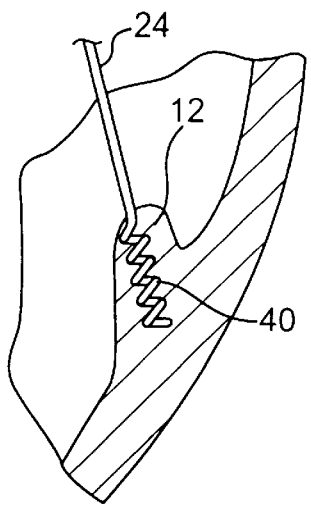
FIG. 19 is a embodiment of a secondary anchor for the device of the present invention.
Figure 20:
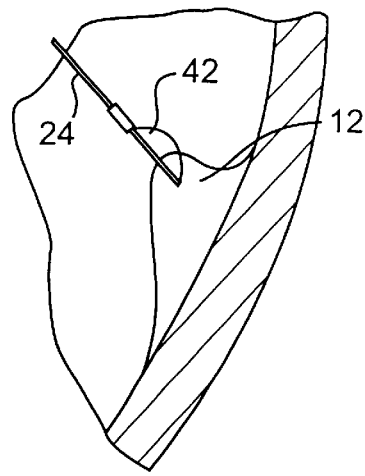
FIG. 20 is a view of an alternate embodiment of a secondary anchor for the device of the present invention.
Figure 21:
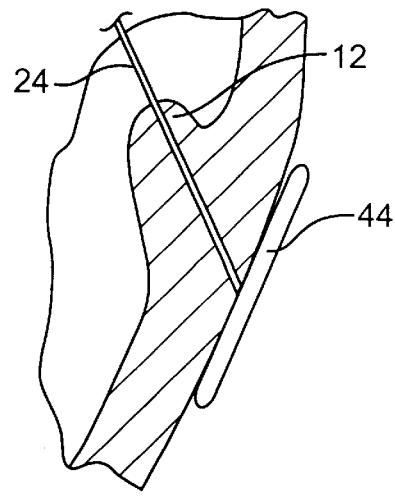
FIG. 21 is yet another embodiment of a secondary anchor for the device of the present invention.

FIGS. 19–21 show various configurations of anchoring devices shown at the second end of tension member 24. It can be appreciated that these anchoring devices could be used with each of the tension members described above. In FIG. 19, the second end of tension member 24 includes a secondary anchor 40 formed as screw which is shown augured into papillary muscle 12. FIG. 20 shows a secondary anchor 42 including a loop sewn through papillary muscle 12. FIG. 21 shows a tension member 24 extending transmurally to an exterior pad 44 to which it is connected. Tension member 24 could be sewn to pad 44 or otherwise mechanically connected thereto.

It can be appreciated that various biocompatible materials can be advantageously used to form the various components of the device of the present invention. It is anticipated that the present device will usually be chronically implanted. Thus, when selecting materials to form each of the components consideration should be given to the consequences of long term exposure of the device to tissue and tissue to the device.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A device for repairing an in situ valve of a heart ventricle, the in situ valve having leaflets and an annulus, the device comprising:

a basal anchor configured to fixedly connect to the in situ valve;

at least one tension member configured to extend from the basal anchor to muscles of the ventricle; and a secondary anchor configured to connect the at least one tension member to muscles of the ventricle.

2. A valve repair device in accordance with claim 1, wherein the basal anchor includes a pad.

3. The device of claim 18, wherein the basal anchor includes an annuloplasty ring.

4. The device of claim 1, wherein the basal anchor includes a suture ring having a varying radius of curvature.

5. A valve replacement device in accordance with claim 1, wherein the secondary anchor includes a hook-shaped papillary muscle tissue loop.

6. A valve repair device in accordance with claim 1, wherein the secondary anchor includes a screw-shaped tissue anchor.

7. The device of claim 1, wherein the basal anchor includes a pair of pads.

8. The device of claim 1, wherein the basal anchor includes a crescent-shaped ring.

9. The device of claim 1, wherein the basal anchor is configured to be sewn to the valve.

10. The device of claim 1, wherein the basal anchor includes an extension adapted to extend through the valve and connect to the at least one tension member.

11. The device of claim 1, wherein the at least one tension member includes a pair of tension members.

12. The device of claim 11, further comprising a third tension member adapted to extend across the ventricle.

13. The device of claim 12, wherein each of the pair of tension members connects to the third tension member.

14. The device of claim 1, wherein the at least one tension member is substantially rigid.

15. The device of claim 1, wherein the at least one tension member is substantially flexible.

16. The device of claim 1, wherein the at least one tension member is configured to reduce a vertical dimension of the ventricle.

17. The device of claim 1, wherein the at least one tension member is configured to reduce a transverse radius of the ventricle.

18. The device of claim 1, wherein the secondary anchor is screw-shaped.

19. The device of claim 1, wherein the secondary anchor includes a loop portion.

20. The device of claim 1, wherein the secondary anchor includes a pad configured to be placed exterior the ventricle.

* * * * *

UNITED STATES PATENT AND TRADEMARK OFFICE
CERTIFICATE OF CORRECTION

PATENT NO.    : 6,332,893 B1
DATED         : December 25, 2001
INVENTOR(S)   : Todd J. Mortier et al.

It is certified that error appears in the above-identified patent and that said Letters Patent is hereby corrected as shown below:

Column 6,
Line 7, replace "claim 18" with -- claim 1 --.

Signed and Sealed this

Thirteenth Day of August, 2002

Attest:

Attesting Officer

JAMES E. ROGAN
*Director of the United States Patent and Trademark Office*